United States Patent [19]

Kaieda et al.

[11] Patent Number: 4,839,290

[45] Date of Patent: Jun. 13, 1989

[54] PROCESS FOR PRODUCING CYTOTOXIC T-CELLS AND COMPOSITIONS PRODUCED BY SAID PROCESS

[75] Inventors: Takeji Kaieda; Kimimasa Yamada; Naokuni Yamawaki, all of Fuji, Japan

[73] Assignee: Asahi Kasei Kogyo Kabushiki Kaisha, Osaka, Japan

[21] Appl. No.: 96,259

[22] Filed: Sep. 8, 1987

Related U.S. Application Data

[63] Continuation of Ser. No. 678,415, Dec. 5, 1984, abandoned.

[30] Foreign Application Priority Data

| Dec. 5, 1983 | [JP] | Japan | 58-228496 |
| May 29, 1984 | [JP] | Japan | 59-107605 |
| Oct. 2, 1984 | [JP] | Japan | 59-205559 |
| Oct. 5, 1984 | [JP] | Japan | 59-208066 |
| Oct. 15, 1984 | [JP] | Japan | 59-214326 |
| Oct. 15, 1984 | [JP] | Japan | 59-214327 |

[51] Int. Cl.$^4$ ............................................. C12N 5/00
[52] U.S. Cl. ............................... 435/240.23; 430/1; 430/2; 430/240.2
[58] Field of Search ............. 424/93; 435/240.23, 435/1, 2, 174, 177, 29; 436/501, 518, 519, 523, 528–534, 813, 822–824, 827, 828

[56] References Cited

U.S. PATENT DOCUMENTS

| 3,999,944 | 12/1976 | Grosser et al. | 436/519 |
| 4,420,481 | 12/1983 | Okazaki et al. | 514/252 |
| 4,426,446 | 1/1984 | Thomson | 436/63 |
| 4,444,887 | 4/1984 | Hoffman | 435/68 |
| 4,455,379 | 6/1984 | Bekesi et al. | 436/504 |
| 4,495,282 | 1/1985 | Ohnishi et al. | 435/68 |
| 4,677,056 | 6/1987 | Dupont et al. | 435/240.27 |
| 4,683,199 | 7/1987 | Palladino | 435/68 |

OTHER PUBLICATIONS

Ashman, R. F., Paul, W. E. et al., ed, *Fundamental Immunology*, Raven Press, N.Y., (1984), pp. 267–300, "Lymphocyte Activation".

Tarmelli, D. et al., *Macrophages and Natural Killer Cells*, Normann, S. J. et al., eds., Plenum Press, N.Y. (1982), pp. 487–492.

Giles, S. et al., Nature 268:154–156 (1977).

Henney, C. S. et al., *Fundamental Immunology*, "Cell-Mediated Cylotoxicity", W. E. Paul, ed., Raven Press, N.Y. (1984), pp. 669–684.

S. Fujimoto et al., J. Immunology, 116 791 (1976).

Y. Ichino et al., Gann, 75 436 (1984).

A. Mazumder et al., The Journal of Immunology, vol. 130, No. 2, 958 (1983).

*Primary Examiner*—Margaret Moskowitz
*Attorney, Agent, or Firm*—Birch, Stewart, Kolasch & Birch

[57] ABSTRACT

A method of inducing antitumor immunocytes which is simple in operation and suitable for inducing antitumor immunocytes having not only excellent cytotoxic activity against tumor cells but also high safety, which method comprises contacting leucocytes with an insoluble, antitumor immunocyte-inducing material capable of linking with T cells, said antitumor immunocyte-inducing material comprising an insoluble carrier and a ligand linked therewith. The induced antitumor immunocytes can be simply separated in substantially ligand-free form from the insoluble, antitumor immunocyte-inducing material. The obtained antitumor immunocytes have not only excellent cytotoxic activity against tumor cells but also high safety.

8 Claims, 1 Drawing Sheet

PROCESS FOR PRODUCING CYTOTOXIC T-CELLS AND COMPOSITIONS PRODUCED BY SAID PROCESS

This application is a continuation, of application Ser. No. 678,415 filed on Dec. 5, 1984, now abandoned.

BACKGROUND OF THE INVENTION

1. Field of the Invention

This invention relates to a method of inducing antitumor immunocytes, and a process for producing antitumor immunocytes and antitumor immunocytes produced by the process. More particularly, the present invention is concerned with a method of inducing antitumor immunocytes which is simple in operation and suitable for inducing antitumor immunocytes having not only excellent cytotoxic activity against tumor cells but also high safety, which method comprises contacting leucocytes with an insoluble, antitumor immunocyte-inducing material capable of binding to T cells, the antitumor immunocyte-inducing material comprising an insoluble carrier and a ligand linked therewith. The present invention is also concerned with a process for producing antitumor immunocytes and antitumor immunocytes produced by the process.

2. Discussion of Related Art

As is well known, it has been reported that cells such as killer T cells, helper T cells, NK cells, activated macrophages and K cells play an important role as antitumor immunocytes in immunological surveillance with respect to malignant tumors in the living body. Based on the above-mentioned knowledge, there has been proposed, as an immunotherapy for malignant tumors, a method comprising activating immunocytes (leucocytes) of patients with malignant tumors to induce the above-mentioned antitumor immunocytes. However, it is known that the immunological activity of patients with malignant tumors is generally lowered with the progress of the tumors, that immunosuppressive factors which suppress the immuno response exist in the living body of patients with malignant tumors and that suppressor T cells and suppressor macrophages are induced in the living body of patients with malignant tumors [S. Fujimoto et al: J. Immunol., 116, 791 (1976)]. In view of the above, it is recognized to be difficult to efficiently induce antitumor immunocytes in the living body of patients with malignant tumors who are under a suppressed state with respect to immunological activity.

In order to eliminate the drawbacks accompanying the above-mentioned method of inducing antitumor immunocytes in the living body of patients with malignant tumors, many researchers have attempted to induce antitumor immunocytes in vitro by activating leucocytes obtained from patients with malignant tumors. For example, there has been proposed a method of inducing killer T cells in vitro which are considered as playing a leading role in antitumor immunity [Y. Ichino et al: Gann(Cancer), 75, 436 (1984)]. In this method, peripheral blood leucocytes obtained from a patient with a malignant tumor are sensitized with tumor cells obtained from the patient to activate the leucocytes for induction of killer T cells which are cytotoxic for tumor cells of the patient but non-cytotoxic for normal cells of the patient. The thus obtained killer T cells are placed back into the living body of the patient. However, killer T cells induced by the above-mentioned in vitro method do not have a cytotoxic activity sufficient to expect a therapeutical effect.

In order to eliminate the drawbacks of the above-mentioned in vitro method, there have been proposed a method in which killer T cells are incubated using a T cell growth factor which is a kind of lymphokine, thereby increasing the quantity of killer T cells, before administering killer T cells to the patient [Y.Ichino et al: Gann(Cancer), 75, 436 (1984)]. This method is hereinafter often referred to as the "incubation method." The mass production of the T cell growth factor to be used in the incubation method has become possible by virtue of genetic manipulation techniques. Therefore, a large quantity of T cell growth factor can be used for the incubation of killer T cells. In view of the above, it seems that the above-mentioned incubation method could be put to a practical use.

However, the incubation method has the following disadvantages.

(1) Whether or not killer T cells can be induced depends on the patients. That is, this method is not necessarily useful with respect to all the patients with malignant tumors.

(2) Killer T cells should be incubated in vitro for a long period of time (generally one to two months). During the incubation the killer T cells tend to be unfavorably degenerated.

(3) Tumor cells of a patient should be used as an antigen for the sensitization of leucocytes. The tumor cells to be used should be obtained in the living state from tumor tissue of the patient by surgery. This is very troublesome.

(4) The obtained tumor cells should behalf-killed with an antitumor compound so that the tumor cells do not grow. The reason for this is as follows. In the incubation method, the mixture of leucocytes obtained from a patient suffering from a malignant tumor with tumor cells obtained from the patient is incubated to induce killer T cells. The induced killer T cells are then incubated using a T cell growth factor. The obtained killer T cells are then administered to the patient. Needless to say, killer T cells to be administered to the patient should not contain living tumor cells. Therefore, half-killed cells should be used for sensitization of leucocytes.

(5) Even though half-killed tumor cells were used for the sensitization of leucocytes there is a danger of living tumor cells being administered to the patient together with killer T cells. This is a serious problem with respect to the incubation method.

As is apparent from the foregoing, the incubation method is disadvantageous not only from the standpoint of ease in operation but also from the standpoint of safety.

SUMMARY OF THE INVENTION

In view of the problems of the conventional methods as mentioned above, the present inventors have made extensive and intensive studies with a view to developing a method of inducing antitumor immunocytes which is simple in operation and suitable for inducing antitumor immunocytes having excellent cytotoxic activity against tumor cells and high safety. Particularly, the present inventors have attempted to induce antitumor immunocytes, especially killer T cells and helper T cells, using an insoluble material which is easy to prepare and handle. Such an attempt to induce antitumor immunocytes using an insoluble material had never been made. However, as a result of extensive and intensive studies, the present inventors have surprisingly found that antitumor immunocytes can be simply and efficiently induced by contacting leucocytes with an insoluble, antitumor immunocyte-inducing material (hereinafter often referred to simply as "insoluble material") capable of binding to T cells, which insoluble material comprises an insoluble carrier and a ligand linked with the insoluble carrier on its surface by means of a covalent bond, that the antitumor immunocytes obtained by activating-human or mouse immunocytes with the above-mentioned insoluble material are highly cytotoxic for tumor cells and that antitumor immunocytes induced by using the above-mentioned insoluble material have no danger of contamination of the antitumor immunocytes with living tumor cells and, hence can be very safely administered to patients with malignant tumor cells.

The present invention has been completed based on such novel findings.

Accordingly, it is an object of the present invention to provide a method of inducing antitumor immunocytes which is simple in operation and suitable for inducing antitumor immunocytes having excellent cytotoxic activity against tumor cells and high safety.

It is another object of the present invention to provide a process for producing antitumor immunocytes having excellent cytotoxic activity against tumor cells and safety.

It is a further object of the present invention to provide antitumor immunocytes produced by the process described above.

The foregoing and other objects, features and advantages of the present invention will be apparent to those skilled in the art from the following detailed description and appended claims taken in connection with the accompanying drawing.

DETAILED DESCRIPTION OF THE INVENTION

In one aspect of the present invention, there is provided a method of inducing antitumor immunocytes which comprises contacting leucocytes with an insoluble, antitumor immunocyte-inducing material capable of binding to T cells, the insoluble, antitumor immunocyte-inducing material comprising an insoluble carrier and a ligand linked with the insoluble carrier on its surface by means of a covalent bond, to activate the leucocytes, thereby converting the leucocytes to antitumor immunocytes.

The present invention will now be described in detail.

In the present invention, the expression "insoluble carrier on its surface" is intended to mean portions of the carrier surface of the insoluble material which are capable of being contacted with leucocytes.

In the present invention, the term "leucocyte" is intended to mean the so-called blood's white cell which are blood cells excluding erythrocytes and thrombocytes and a cell fraction obtained by removing granulocytes and/or B cells from the so-called blood's white cells. In the present invention blood's white cells containing as its component at least T cells and macrophages may be used as leucocytes. As examples of the leucocytes which may be preferably used in the present invention, there may be mentioned a leucocyte fraction obtained from peripheral blood by the continuous centrifugation method, a mononuclear cell fraction obtained by the Ficoll-Paque centrifugation method [Pharmacia Fine Chemicals Catalogue 84, p.90 issued by Pharmacia Fine Chemicals AB, Sweden] and a T cell fraction obtained by the method in which peripheral blood mononuclear cells are subjected to rossette formation with neuramidase-treated sheep erythrocytes to separate and concentrate the T cell fraction. By the use of the above-mentioned leucocytes there can be induced antitumor immunocytes having a high cytotoxic activity against tumor cells.

The leucocytes to be used in the present invention may be any of those which have been obtained from patients with malignant tumors and normal human beings. But, there may be preferably used leucocytes from a patient with a malignant tumor to whom antitumor immunocytes to be obtained is to be administered.

The antitumor immunocytes induced according to the method of the present invention belong to a lymphocyte fraction, i.e. leucocyte fraction excluding granulocytes, monocytes and macrophages and, especially, has properties of T cells:

The insoluble, antitumor immunocyte-inducing material to be used in the present invention comprises an insoluble carrier and a ligand linked with the insoluble carrier on its surface by means of a covalent bond. It is required that the insoluble, antitumor immunocyte-inducing material to be used in the present invention be an insoluble material capable of binding to T cells. Whether or not an insoluble material can be used in the present invention as antitumor immunocyte-inducing material may be determined by the following test. $1 \times 10^6$ T cells are suspended in 1 ml of RPMI 1640 medium containing 10% by volume of fetal calf serum to form a suspension. 100 μl of an insoluble material to be tested is added to the suspension. The resulting mixture is subjected to centrifugation and then kept at 37° C. for 20 hours. After 20 hours, the mixture is gently stirred and the resulting supernatant is then removed. The thus treated insoluble material is subjected to microscopic examination to determine whether or not the insoluble material has T cells linked therewith. T cells to be used in the test described above are preferably those derived from human beings, more preferably those derived from patients with malignant tumors.

It is preferred that the antitumor immunocyte-inducing material to be used in the present invention be an insoluble material capable of binding, to 1% or more of T cells used in the test described above. However, when the insoluble material comprises an insoluble carrier and, linked with the carrier, a tumor-associated antigen, the insoluble material capable of binding to 0.01% or more of the T cells used in the test described above may be used in the present invention as antitumor immunocyte-inducing material.

In the insoluble, antitumor immunocyte-inducing material to be used in the present invention, the ligand linked with the insoluble carrier on its surface may be of any kind as long as the antitumor immunocyte-inducing material comprising an insoluble carrier and the ligand linked therewith is capable of binding to T cells in the above-mentioned test. As examples of the ligand, there may be mentioned a T lymphocyte-activating substance, an antigenic substance, a hydrophobic substance and an anionic substance. Of the above-mentioned ligands, the T lymphocyte-activating substance per se is able to activate leucocytes to induce antitumor immunocytes. However, the antitumor immunocytes induced by using an antitumor immunocyte-inducing material comprising an insoluble carrier and as ligand a T lymphocyte-activating substance are higher in cytotoxic activity against tumor cells than the antitumor immunocytes induced by the lymphocyte-activating substance per se, i.e. the lymphocyte-activating substance not linked with an insoluble carrier.

As examples of preferable T lymphocyte-activating substances, there may be mentioned a lectin, a lymphokine such as interleukin 2 or γ-interferon, anti-T cell antibodies and their fragments such as anti-idiotype antibodies and protein A. A lectin and protein A are more preferable. Of the protein A, protein A derived from *Staphylococcus aureus* is preferable. As examples of the lectin, there may be mentioned a red kidney bean lectin (PHA) derived from *Phaseolus vulgaris*, a concanavalin A (Con A) derived from *Concanavalia ensiformis*, a lectin (WFA) derived from *Wistaria aoribanda*, a lentil lectin (LCH) derived from *Lens culinaris*, a pokeweed mitogen (PWM) derived from *Phytolacca americana*, a soybean lectin (SBA) derived from *Glycine max*, a lima-bean lectin (LBA) derived from *Phaseolus Lunatus*, a false acacia lectin (RPA) derived from *Robina pseudoacacia*, a lectin (SJA) derived from *Sophora Japonica*, a pea lectin (PSA) derived from *Pisum sativum*, a broad bean lectin (VFA) derived from *Vicia faba* and the like. Of them, PHA, Con A, WFA, LCH and PWM are more preferable in view of cytotoxic activity of antitumor immunocytes induced.

As the antigenic substance linked, as a ligand, with the insoluble carrier, there may be mentioned tumor-associated antigens existing on the membrane of tumor cells, oligosaccharides and peptides which are antigenic determinants of gangliosides and glycoproteins related to tumor antigen. Of them, oligosaccharides exhibit a especially high capacity for inducing antitumor immunocytes. The oligosaccharide linked with the carrier may be one which is composed of at least two members selected from the group consisting of N-acetylglucosamine, N-acetylgalactosamine, galactose, fucose, mannose, glucose and N-acetylneuraminic acid. For example, the oligosaccharide linked with the carrier may be an oligosaccharide composed of N-acetylneuraminic acid, galactose, N-acetylglucosamine and fucose or an oligosaccharide composed of galactose, N-acetylglucosamine and fucose. Further, the oligosaccharide may be The oligosaccharides having too large a molecular weight are difficult to prepare. Therefore, the molecular weight of the oligosaccharides is generally 10,000 or less, preferably 5,000 or less, more preferably 2,000 or less. With respect to the oligosaccharides of which the structure is unknown and/or the oligosaccharides which have high molecular weight, the molecular weight of such compounds is determined by the gel permeation chromatography [see "Biochemistry Data Book II" edited by Nihon Seikagakukai, Tokyo Kagakudozin, P. 1187~] and expressed in terms of weight average molecular weight.

In the present invention, there may be used an insoluble, antitumor immunocyte-inducing material comprising an insoluble carrier and, linked with the carrier, an oligosaccharide obtained from the mucous membrane of animals, which shows excellent capacity for inducing antitumor immunocytes. The insoluble, antitumor immunocyte-inducing material to be used in the present invention is not restricted to the above-mentioned material. Any insoluble, antitumor immunocyte-inducing material which comprises an insoluble carrier and an oligosaccharide linked with the carrier can be employed as the insoluble, antitumor immunocyte-inducing material showing good capacity, for inducing antitumor immunocytes.

As the hydrophobic substance linked, as a ligand, with the insoluble carrier, there may be mentioned compounds having at least one aromatic ring, which produce preferable results. The term "aromatic ring" is intended to mean a cyclic compound having aromatic characteristics. Compounds having any aromatic ring may be the hydrophobic substance. As preferred examples of the compounds having at least one aromatic ring there may be mentioned hydrophobic organic compounds having at least one member selected from benzene type aromatic rings such as benzene, naphthalene and phenanthrene; nitrogen-containing 6-membered rings such as pyridine quinoline, acridine, isoquinoline and phenanthridine; nitrogen-containing 5membered rings such as indole, carbazole, isoindole, indolizine, porphyrin and 2,3,2',3'-pyrrolopyrrole; polyvalent nitrogen-containing 6-membered rings such as pyridazine, pyrimidine, sym-triazine, sym-tetrazine, quinazoline, 1,5-naphthyridine, butylidyne and phenazine; polyvalent nitrogen-containing 5-membered rings such as pyrazole, 1,2,4-triazole, 1,2,3-triazole, tetrazole, benziminazole, imidazole and purine; norharman ring; perimidine ring; oxygen-containing aromatic rings such as benzofuran, isobenzofuran and dibenzofuran; sulfur-containing aromatic rings such as benzothiophene and thienothiophene; oxygen-containing heteroaromatic rings such as oxazole, isoxazole, 1,2,5-oxadiazole and benzoxazole; sulfur-containing heteroaromatic rings such as thiazole, isothiazole, 1,3,4-thiadiazole and benzthiazol; and derivatives thereof. As more preferred examples of the compounds having at least one aromatic ring, there maybe mentioned chemically modified or unmodified nucleic acid-constituting bases, chemically modified or unmodified nucleosides and chemically modified or unmodified nucleotides. Examples of the nucleic acid-constituting bases are adenine, 1-methyladenine, 2-methyladenine, N-(purine-6-ylcarbamoyl)-L-threonine, $N^6$-($\Delta^2$-isopentenyl)adenine, 2-methylthio-$N^6$-($\Delta^2$-isopentenyl)adenine, 2-hydroxyadenine, $N^6$-methyladenine, $N^6,N^6$-dimethyladenine, $N^6$-(cis-4-hydroxyisopentenyl)adenine, zeatin, 2-aminoadenine, guanine, 1-methylguanine, $N^2$-methylguanine, $N^2,N^2$-dimethylguanine, 7-methylguanine, cytosine, 3-methylcytosine, $N^4$-acetylcytosine, $N^4$-methylcytosine, 5-methylcytosine, 5-hydroxymethylcytosine, 2-thiocytosine, uracil, thymine, 4-thiouracil, 5-hydroxyuracil, 5-hydroxymethyluracil, 5-methoxyuracil, 5-carboxymethyluracil, 2-thiothymine, 5-carboxymethyl-2-thiouracil, 5-(methoxycarbonylmethyl)-2-thiouracil, 5-(N-methylaminomethyl)-2-thiouracil, 5,6-dihydrouracil, 5,6-dihydrothymine, 5-(4-aminobutylaminomethyl)uracil, S(+)5-(4,5-dihydroxypentyl)uracil, orotic acid, wye, wybutine, peroxywybutine, hypoxanthine, 1-methylhypoxanthine, xanthine, uric acid and the like. As examples of the nucleosides, there may be mentioned adenosine, 2-methyladenosine, guanosine 1-methylguanosine, inosine, cytidine, uridine and the like. As examples of the nucleotides, there may be mentioned adenosine 3'-phosphate, guanosine 3'-phosphate, cytidine 3'-phosphate, uridine 3'-phosphate and the like. Of the above, nucleic acid-constituting bases produce the most preferable results. The nucleic acid-constituting bases, nucleosides, nucleotides and derivatives thereof which have too large a molecular weight are difficult to prepare. Therefore, the molecular weight of the nucleic acid-constituting bases, nucleosides, nucleotides and derivatives thereof is generally 10,000 or less, preferably 5,000 or less, more preferably 2,000 or less. With respect to the nucleic acid-constituting bases, nucleosides, nucleotides and derivatives thereof of which the structure is unknown and/or the nucleic acid-constituting bases, nucleosides, nucleotides and derivatives thereof which have a high molecular weight, the molecular weight of such compounds is determined by gel permiation chromatography [see "Biochemistry Data Book II" edited by Nihon Seikagakukai, Tokyo Kagakudozin, P. 1187~] and expressed in terms of weight average molecular weight.

As the anionic substance linked, as a ligand, with the insoluble carrier, any compounds having an anionic group or anionic groups may be mentioned. Preferably, there may be mentioned compounds having at least one member selected from a sulfonic group, carboxyl group, phosphoric acid group, arsonic acid group, selenonic acid group and the like. Compounds having at least one member selected from a sulfonic group carboxyl group and phosphoric acid group are more preferred. In the present invention, as the insoluble, antitumor immunocyte-inducing material, for example, there may be employed insoluble materials prepared by linking a synthetic anion compound and/or a natural anion compound and/or a polyanion compound as a ligand to the insoluble carrier. Further, there may be used sulfonic acid type cation exchangers, carboxylic acid type cation exchangers and phosphoric acid type cation exchangers.

In the present invention, as the anion compounds, there may also be mentioned compounds capable of introducing a silanol group or silanol groups into an insoluble carrier.

Examples of the anion compounds are as follows. (1) Compounds having a sulfonic group:

There may be mentioned chlorosulfonic acid and derivatives; isethionic acid and derivatives thereof as a compound having not only a sulfonic group but also a hydroxyl group; sulfonacetic acid and derivatives thereof as a compound having not only a sulfonic group but also a carboxyl group; sulfamic acid, taurine, anilinesulfonic acid, aminotoluenesulfonic acid, o-(2-aminoethylamine)-1-naphthalenesulfonic acid and derivatives thereof as a compound having not only a sulfonic group but also an amino group.

(2) Compounds having a carboxyl group:

There may be mentioned as a compound having a carboxyl group acetic acid halogenide and derivatives thereof; as a compound having not only a carboxyl group but also a hydroxyl group, hydroxyacetic acid, lactic acid, hydroxybutyric acid, hydroxyisocaproic acid, 2-ethyl-hydroxybutyric acid, hydroxyacrylic acid, hydroxystearic acid, glyceric acid, hydroxymalonic acid, malic acid, racemic acid, tartaric acid, saccharic acids such as D-gluconic acid, D-mannoic acid, D-galactonic acid, D-glucuronic acid, D-galacturonic acid, D-glucosaccharic acid and galactaric acid, and derivatives thereof; as a compound having not only a carboxyl group but also an amino group, amino acids and derivatives thereof such as glycine, sarcosine, alanine, aminobutyric acid, α-aminovaleric acid, valine, leucine, isoleucine, serine, cysteine, cystine, methionine, ornithine, lysine, algin, alginic acid, aspartic acid and glutamic acid.

As a compound having not only a carboxyl group but also an epoxy group, there may be mentioned epihydrinic acid, epoxystearic acid, 12,13-epoxyoleic acid and derivatives thereof.

As a compound having not only a carboxyl group but also an aldehyde group, there may be mentioned glyoxylic acid, formylacetic acid, 3-formylpropionic acid and derivatives thereof.

As a compound having not only a carboxyl group but also a mercapto group, there may be mentioned mercaptoacetic acid, thiomalic acid and derivatives thereof.

As a compound having not only a carboxyl group but also a cyano group, there may be mentioned cyanoacetic acid, 2-cyanopropionic acid and derivatives thereof.

(3) Compound having a phosphoric acid group:

There may be mentioned as a compound having a phosphoric acid group or groups diphosphorus pentoxide, o-carboxyphenyl phosphate, oxymethylphosphonic acid and derivatives thereof.

(4) Compound having a arsonic acid group:

There may be mentioned, as a compound having an arsonic acid group o-arsanilic acid, p-arsanilic acid, arsonoacetic acid, p-hydroxyphenylarsonic acid, β-hydroxyethylarsonic acid and derivatives thereof.

(5) Compound capable of introducing a silanol group:

As a compound capable of introdung a silanol group or silanol groups to an insoluble carrier, there may be mentioned 3-aminopropyltriethoxysilane, 3-(2-aminoethylaminopropyl)dimethoxymethylsilane, 3-(2-aminoethylaminopropyl)trimethoxysilane or the like. Such compound is bonded to an insoluble carrier through its amino group, and the methoxy group or ethoxy group is hydrolyzed, thereby to obtain an insoluble carrier having a silanol group.

As the polyanion compounds, there may be mentioned, for example, acidic polysaccharides such as heparin, dextran sulfate, polygalacturonic acid, mannan phosphate, chondroitin, chondroitin sulfate A, chondroitin C, hyaluronic acid, alginic acid, pectic acid and fucanic acid; natural high polymers and derivatives thereof, such as carboxymethylcellulose, cellulose sulfate, carboxymethyl starch, cellulose phosphate and derivatives thereof; synthetic polyanion compounds prepared by polymerization such as polyacrylic acid, polymethacrylic acid, polyvinyl sulfate, polystyrene sulfonate, copolymers containing maleic acid as a co-monomer, polyphosphoric acid, polyvinyl phosphoric acid, polystyrene phosphoric acid, polyglutamic acid, polyaspartic acid, esters of polyphosphoric acid, and derivatives thereof. In the present invention, the anion compounds and polyanion compounds are not restricted to those as mentioned above.

In the case in which an anion compound and/or a polyanion compound are fixed to a carrier, the anionic group density of the insoluble, antitumor immunocyte-inducing material to be used in the present invention is preferably 0.2 $\mu$eq ($0.2 \times 10^{-6}$ equivalent) per m$^2$ of the insoluble material to 2 meq ($2 \times 10^{-3}$ equivalent) per m$^2$ of the insoluble material from the standpoint of a sufficient, specific electrostatic interaction between leucocytes and the insoluble, antitumor immunocyte-inducing material.

The anionic group density of the insoluble, antitumor immunocyte-inducing material is more preferably 2 $\mu$eq/m$^2$ to 1 meq/m$^2$, still more preferably 5 to 500 $\mu$eq/m$^2$. The anionic group density of the insoluble, antitumor immunocyte-inducing material may be determined according to the ordinary method for determining the ion exchange capacity of a cation exchange resin [see "DIAION ION EXCHANGE RESIN.SYNTHETIC ADSORBENT MANUAL [I]" published by Mitsubishi Chemical Industries Limited, pp. 95~101 (1982)].

The anion compounds and polyanion compounds which have too large a molecular weight are difficult to prepare. Therefore, the molecular weight of the anion compounds and/or polyanion compounds is preferably 10,000 or less, more preferably 5,000 or less, most preferably 2,000 or less.

With respect to the molecular weight of the polyanion compounds which have a high molecular weight, the molecular weight of such compounds is determined by gel filtration high speed liquid chromatography [see "Biochemistry Data Book II" edited by Nihon Seikagakukai, Tokyo Kagakudozin, pp. 1212~1215 (1980)] and expressed in terms of weight average molecular weight.

In the case in which the insoluble, antitumor immunocyte-inducing material comprising an insoluble carrier and a polyanion compound is used, it is preferred that the polyanion compound have at least one anionic group per 1,000 in weight average molecular weight of the polyanion compound, more preferably one or more anionic group per 500 in weight average molecular weight of the polyanion compound, still more preferably one or more anionic group per 300 in weight average molecular weight of the polyanion compound. The "molecular weight of the polyanion compound" means that including the molecular weight of the anionic group or groups of the polyanion compound.

As the polyanion compound, not only any natural polyanion compounds but also any synthetic polyanion compounds may be mentioned. Especially, synthetic polyanion compounds are advantageous as compared with natural polyanion compounds. Illustratively stated, the synthetic polyanion compounds are excellent in chemical stability and it is easy to prepare synthetic polyanion compounds which are stable to high-pressure steam sterilization, gamma ray sterilization, ethylene oxide gas sterilization and the like. Therefore, the synthetic polyanion compounds are especially useful for clinical use or when aseptic operations are needed. Further, since it is easy to regulate the anionic group density of the synthetic polyanion compounds, an insoluble material which can effectively induce antitumor immunocytes can be produced with high reproducibility.

The insoluble, antitumor immunocyte-inducing material to be used in the present invention may be those comprising an insoluble material and, fixed herewith, the above mentioned ligands (T lymphocyte-activating substances, antigenic substances, hydrophobic substances and anionic substances), either alone or in any combination.

The above-mentioned oligosaccharides, nucleic acid-constituting bases, anionic groups and the like per se have no capacity for inducing antitumor immunocytes. However, they have a capacity for inducing antitumor immunocytes under a condition that they are linked with an insoluble carrier.

In the present invention, the insoluble carrier linked with a ligand may be hydrophilic or hydrophobic.

The terminology "insoluble carrier" as used herein indicates that the carrier is not soluble in any medium, serum, plasma, physiological salt solution such as physiological saline and the like to be employed in the present invention. In some cases, however, a hydrophilic carrier is preferred, since the use of a hydrophobic carrier may be accompanied by a breakdown of the ligand structure due to the adsorption of coexistent protein thereonto, which causes the resulting autitumor immunocyte-inducing material to have a decreased capacity for inducing antitumor immunocytes. The form of the insoluble carrier is not particularly critical, and any of a number of known forms may be used. For example, there may be mentioned particulate, fibrous hollow fiber and filmy forms. Among these forms, particulate forms are preferred since a large surface area per unit volume may be given by particulate forms. When a particulate, e.g. spherically particulate insoluble carrier is used, it is preferred that the carrier have a particle diameter of from 1 to 3000 microns. A carrier having a particle diameter of less than 1 micron is disadvantageous because it becomes difficult to separate antitumor immunocytes from the carrier. The particle diameter of the carrier may be more preferably 50 microns or more, still more preferably 80 microns or more from the viewpoint of facilitating the separation by filtration of antitumor immunocytes from the carrier. On the other hand, a carrier having a particle diameter of more than 300 microns is also disadvantageous because the surface area per unit weight of the carrier over which leucocytes contact the carrier is reduced. The particle diameter of the carrier may be more preferably 2000 microns or less. With respect to the specific gravity of the particulate, e.g. spherically particulate carrier, a carrier having a specific gravity of 1.07 or more may be desirable because separation of antitumor immunocytes by centrifugation or standing is facilitated with such a carrier. When the carrier is a fibrous carrier, it is preferred that the diameter of the fibrous carrier be in the range of from 0.1 to 3000 microns, especially from 1 to 2000 microns, more especially from 5 to 1000 microns. Both a fibrous carrier having a diameter of less than 0.1 micron and a fibrous carrier having a diameter of more than 3000 microns are disadvantageous because they produce antitumor immunocyte-inducing materials having an insufficient capacity for inducing antitumor immunocytes. When the carrier is a filmy or hollow fibrous porous carrier, it is preferred that the carrier have a pore diameter of from 0.05 to 10 microns through which cells cannot be passed but the contact medium can be freely passed. The reason is that such a carrier permits the contact medium to be fed from one side of the carrier to the leucocytes bonded to the other side of the carrier so that it is possible to activate leucocytes at a high concentration. Filmy or hollow fibrous porous carriers having a pore diameter of from 0.1 to 5 microns are more preferred. The thickness of the filmy carrier and the wall thickness of the hollow fibrous carrier may each be preferably in the range of from 0.1 to 1000 microns.

The insoluble carrier generally has a surface area per unit volume of from $10^{-2}$ to $10^5$ mm$^2$/mm$^3$ as measured according to the below-described method. A carrier having a surface area smaller than $10^{-2}$ mm$^2$/mm$^3$ is not suitable because it causes the capacity of the ultimate material for inducing antitumor immunocytes to be decreased. Generally, the larger the surface area of the carrier, the greater the capacity of the ultimate material for inducing antitumor immunocytes. However, it is generally not feasible to produce a carrier having a surface area greater than $10^5$ mm$^2$/mm$^3$. The surface area per unit volume of a particulate carrier may be determined by measuring the weight average particle diameter according to the method described in the book "Ryudo-Sokutei-Gijutsu (Granulometry Technology)" published by the Nikkan Kogyo Shimbun, Ltd., Tokyo, Japan in 1975, starting on page 69, and calculating a surface area assuming that the particles are spherical. The surface area per unit volume of a fibrous carrier may be determined by weighing a sample having a predetermined length, dividing the weight by the specific gravity of the carrier to obtain the volume of the sample, and calculating from the obtained volume assuming that the fibrous carrier is cylindrical. The surface area per unit volume of a filmy carrier may be determined by weighing a sample having a predetermined area, dividing the weight by the specific gravity of the carrier to obtain the volume of the sample, and calculating the surface area per unit volume. The surface area per unit volume of a hollow fibrous carrier may be determined in a manner similar to that described above with respect to the determination of the surface area per unit volume of a fibrous carrier.

The material of the carrier is not critical, and the carrier may be composed of an inorganic material, a natural polymer, a synthetic polymer or a mixture thereof. As the suitable inorganic material, there may be mentioned, for example, an activated carbon, a glass and materials obtainable by modification thereof. As the suitable natural polymer, there may be mentioned, for example, simple polysaccharides such as cellulose, agarose, dextran and starch, and a mixture thereof. Further, as the suitable synthetic polymer, there may be mentioned, for example, vinyl homopolymers and copolymers such as those obtained by homopolymerizing or copolymerizing at least one member selected from the group consisting of styrene, vinyl acetate, methacrylic esters, acrylic esters, halogenated vinyl compounds, halogenated vinylidene compounds, acrylonitrile, acrylamide, methyl vinyl ketone, vinylpyrrolidone, 2-vinylpyridine, ethylene, propylene, butadiene, isoprene and derivatives thereof; homopolymers and copolymers obtained by effecting ring-opening home-polymerization or copolymerization of at least one member selected from the group consisting of dimethylcyclopropane, spiro-di-o-xylylene, norbornene, cyclopolysiloxane, phosphonitrile chloride, N-carboxy-α-amino acid anhydrides and derivatives thereof as well as polyformaldehyde, polyethyleneoxide, polypropylene glycol, poly-3,3-bis(chloromethyl) oxacyclobutane, polytetrahydrofuran, polycaprolactam and derivatives thereof; condensation polymers such as polyesters, polyamides, polyanhydrides, polycarbonate, polyurea, polysulfonamides, polyimides, polybenzoimidazole and derivatives thereof; fluoropolymers; polyurethane; and resins such as epoxy resin, urea resin, amino resin, melamine resin, silicone resin, alkyd resin and derivatives thereof.

The above-mentioned polymers, i.e. natural and synthetic polymers and mixtures thereof, may be insolubilized according to need by the use of a comonomer or a crosslinking agent to obtain an insoluble carrier. A suitable crosslinking agent may be selected, in accordance with the functional groups of the polymer to be crosslinked, from sulfur, organic peroxides, phenol resins, diisocyanate componds, epoxy compounds, diene compounds, glutaraldehydes and the like. In this connection, reference may be made to pages 3 to 77 of the Crosslinking Agent Handbook published by Taisei-sha, Tokyo, Japan in 1981.

Moreover, in the present invention, the carrier may be one having a multi-layer structure, which is obtained, for example, by providing the above-mentioned insoluble carrier with a polymer coating. For example, the carrier may be one obtained by providing an activated carbon or glass bead with a polyhydroxyethyl methacrylate coating.

In another aspect of the present invention, there is provided a process for producing antitumor immunocytes comprising:

contacting leucocytes with an insoluble, antitumor immunocyte-inducing material capable of binding to T cells, the insoluble, antitumor immunocyte-inducing material comprising an insoluble carrier and a ligand linked with the insoluble carrier on its surface by means of a covalent bond, to activate the leucocytes, thereby converting the leucocytes to antitumor immunocytes; and separating the antitumor immunocytes from the insoluble, antitumor immunocyte-inducing material, thus obtaining the antitumor immunocytes in substantially ligand-free form.

In the present invention, it is required that the ligand such as the T lymphocyte-activating substance, antigenic substance, hydrophobic substance, anionic substance or the like be linked to the surface of an insoluble carrier by means of a covalent bond. Antitumor immunocytes can be obtained in substantially ligand-free form by using the antitumor immunocyte-inducing material comprising an insoluble carrier and a ligand linked with the surface of the insoluble carrier by means of a covalent bond. For linking the ligand with the surface of the insoluble carrier by means of a covalent bond, the customary techniques for activating a carrier and bonding a ligand that have been generally used for fixation of enzymes and affinity chromatography may be employed in the present invention. For example, a ligand may be linked with an agarose gel as the carrier, by activating the gel with cyanogen bromide to obtain an activated gel and reacting the ligand with the thus obtained activated gel. Further, a ligand may be linked with a silica glass in the form of beads, by reacting γ-aminopropyltriethoxysilane with the glass to obtain an alkylaminoglass, activating the alkylaminoglass with a glutaraldehyde and reacting the resulting activated glass with the ligand. Moreover, according to need, a molecule having an arbitrary length may be incorporated, as a spacer, between an insoluble carrier and a ligand. For example, a spacer may be incorporated by reacting one terminal isocyanate group of hexamethylene diisocyanate with a hydroxyl group of agarose and then reacting the other terminal isocyanate group of the diisocyanate with the amino group of a ligand such as nucleic acid-constituting base, nucleoside, nucleotide or the like.

In the present invention, it is preferred that the density of the ligand over the surface of the insoluble carrier be in the range of from $10^5$ to $10^{12}$ molecules/mm$^2$, especially from $10^6$ to $10^{11}$ molecules/mm$^2$, more especially from $10^7$ to $10^{10}$ molecules/mm$^2$ from the standpoints of the capacity of the antitumor immunocyte-inducing material for inducing antitumor immunocytes and economy.

With respect to the molecular weight of the ligand, it is preferred that the molecular weight of the T lymphocyte-activating substance be not greater than 200,000, especially 150,000 from the standpoint of the capacity of the antitumor immunocyte-inducing material for inducing antitumor immunocytes. Meanwhile, it is preferred that other types of ligands such as the oligosaccharide, nucleic acid-constituting base and anionic substance have a molecular weight of 10,000 or less, especially 5,000 or less, more especially 2,000 or less from the standpoints of ease of the synthesis and the capacity of the antitumor immunocyte-inducing material for inducing antitumor immunocytes.

There have been described above the representative processes for preparing the antitumor immunocyte-inducing material to be employed in the present invention, in which a carrier is first activated and then a ligand is reacted with the resulting activated carrier to link the ligand with the carrier. However, the processes for preparing the antitumor immunocyte-inducing material to be employed in the present invention are not limited to the above processes. For example, the antitumor immunocyte-inducing material to be employed in the present invention may be prepared by a process comprising first linking a ligand with a monomer and then polymerizing the monomer, or by a process comprising first activating a ligand and then linking the resulting activated ligand with an insoluble carrier. Basically, the antitumor immunocyte-activating material to be employed in the present invention exhibits its advantageous effects when it is in such a state that at least one kind of ligand such as T lymphocyte-activating substance, oligosaccharide, nucleic acid-constituting base, anionic substance, chemically modified derivative thereof or the like is linked with the surface of an insoluble carrier.

In the present invention, the leucocytes may be subjected to an immunosuppressor cell-removing treatment before the activation thereof. Known immunosuppressor cells are suppressor T cells and suppressor macrophages. Suppressor T cells may be removed from the leucocytes by a method in which an antibody to the suppressor T cells is added to a leucocyte suspension to coagulate the suppressor cells, or by a method in which the leucocytes are contacted with a material comprising an insoluble carrier and, bonded thereto, such an antibody, histamine or other agent having capacity for removing the suppressor cells to remove the suppressor cells. Of them, the latter method is preferred because the treated-leucocytes are not contaminated with the antibody. On the other hand, suppressor macrophages may be removed from the leucocytes by a method in which a known insoluble carrier, such as glass beads and polystyrene beads, having a capacity for specifically adsorbing the monocytes containing the suppressor macrophages or a material comprising an insoluble carrier and, bonded thereto, an antibody to the monocyte is used to remove the monocytes containing the suppressor macrophages. Alternatively, suppressor macrophages may be removed from the leucocytes by a known method in which powdery iron or the like is contacted with the monocytes containing the suppressor macrophages. It is to be noted that, if the monocytes are completely removed, the activation of antitumor immunocytes is hindered. Therefore, it is necessary that an appropriate amount of monocytes be left unremoved. It is preferred that the above monocyte-removing treatment be effected to such an extent that the monocyte concentration relative to the total number of the leucocytes becomes in the range of from 0.2 to 1.0%, especially from 0.3 to 0.6%, and that addition of fresh leucocytes in an amount of from 3 to 20% relative to the number of the leucocytes to which fresh leucocytes are added follows the monocyte-removing treatment. In the present invention, the immunosuppressor cells may be lysed by contacting the cells with an antibody to the cells and a complement. As the suitable antibody and complement, there may be mentioned, for example, commercially available antisera and antibodies and the complements from rabbit, guinea pig, human and the like.

In the present invention, extremely active antitumor immunocytes may be effectively induced by contacting leucocytes with the antitumor immunocyte-inducing material in a medium (hereinafter referred to as "contact medium") in which a serum is contained. As the suitable contact medium, there may be mentioned, for example, media generally employed to incubate animal cells, such as RPMI 1640 medium and MEM medium, to which an animal serum such as fetal calf serum, bovine serum, equine serum or the like or a human serum is added in an amount of from 2 to 20% by volume. In place of the above sera, components thereof, such as serum albumin, may be added to RPMI 1640 medium to prepare a suitable contact medium. Antitumor immunocytes having an increased activity may be induced by effecting the activation of the leucocytes in a contact medium to which interleukin 2 is added.

In the present invention, leucocytes that may be harvested in various manners may be suspended in the above-mentioned contact medium at a concentration of from $0.5 \times 10^6$ to $3 \times 10^6$ cells/ml. Then, a predetermined amount of an antitumor immunocytes-inducing material may be added to the suspension, and incubation may be performed at a temperature of from 25° to 45° C. When the incubation is performed at a temperature lower than 25° C., little effective activation of the leucocyte occurs. On the other hand, when the incubation is performed at a temperature higher than 45° C., the survival rate of the leucocytes becomes low. Incubation of the leucocytes to induce antitumor immunocytes according to the present invention may be performed in a commercially available plastic vessel generally employed for cell culture which is placed in a $CO_2$ incubator. Leucocytes may be adsorbed onto the antitumor immunocyte-inducing material and begin to be activated within an incubation period of several hours.

The incubation period varies widely according to the incubation temperature, concentration of leucocytes suspended in a contact medium and the like, but is generally 4 hours to 5 days.

In the present invention, whilst T cells strongly bind to an antitumor immunocyte-inducing material, the resulting antitumor immunocytes weakly bind to the material or detach themselves from the material. The antitumor immunocytes which weakly bind to the material can be readily separated from the material by shaking the vessel containing the material or other mechanical means. For example, the induced antitumor immunocytes may be separated from an antitumor immunocyte-inducing material by subjecting the suspension containing the material having the immunocytes linked therewith to pipetting (repeating gentle drawing-in and -out of a pipette) and allowing the suspension to stand still for a period of 1 to 3 minutes to obtain the antitumor immunocytes as the supernatant. When an antitumor immunocyte-inducing material having a lectin linked therewith is employed, separation of the induced antitumor immunocytes from the material may be readily attained by adding to the suspension containing the material a physiological saline containing a saccharide capable of binding to the lectin. For example, when an antitumor immunocyte-inducing material having concanavalin A linked therewith is employed, separation of the induced antitumor immunocytes from the material may be attained by adding to the suspension containing the material a physiological saline containing α-methylmannose. As described above, separation of the induced antitumor immunocytes from the antitumor immunocyte-inducing material may be readily attained by physical and/or chemical means.

In a further aspect of the present invention, there are provided antitumor immunocytes which are produced by a process comprising :

contacting leucocytes with an isoluble, antitumor immunocyte-inducing material capable of binding to T cells, the insoluble, antitumor immunocyte-inducing material comprising an insoluble carrier and a ligand linked with the insoluble carrier on its surface by means of a covalent bond, to activate the leucocytes, thereby converting the leucocytes to antitumor immunocytes; and separating the antitumor immunocytes from the insoluble, antitumor immunocyte-inducing material, thus obtaining the antitumor immunocytes in substantially ligand-free form.

It has been found that the leucocytes activated by the above-mentioned process contain cells having a capacity for effectively lysing tumor cells. In particular, as a result of an application test to human tumor cells, it has been found that the human peripheral blood leucocytes activated using an antitumor immunocyte-inducing material as defined herein effectively lyse the MKN-1 gastric cancer cells and PC-10 lung cancer cells. Moreover, the BALB/c mouse spleen leucocytes activated using an antitumor immunocyte-activating material as defined herein effectively lysed the Colon 26 (BALB/c derived syngeneic tumor) and B-16 (C57/B16 melanoma).

With respect to the antitumor immunocytes obtained according to the present invention, even if the leucocytes are activated by an antitumor immunocyte-inducing material having an isotope-labeled T lymphocyte-activating substance linked therewith, the resulting antitumor immunocytes do not have a detectable radioactivity. This indicates that in the present invention, antitumor immunocytes can be obtained in ligand-free form, i.e. safe antitumor immunocytes are obtained even if an antitumor immunocyte-inducing material has a T lymphocyte-activating substance linked therewith which is hazardous to humans. As a result of an in vivo test using syngeneic tumor-bearing mice, it has been found that the antitumor immunocytes of the present invention can completely prevent the growth of the tumor cells. From this, it is expected that in the case of a clinical application, translocation of the tumor cells will be completely prevented by administering about $10^8$ to $10^9$ antitumor cells obtained according to the present invention several times a week to a cancer patient after the enucleation of the tumor.

Figure 1:
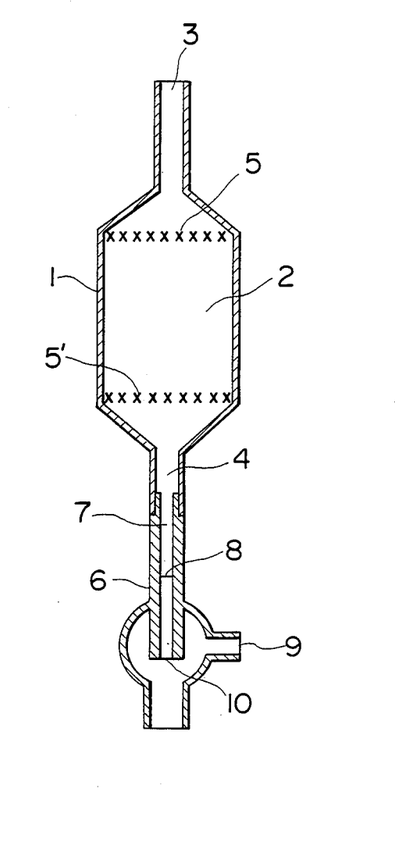
The FIGURE shows a diagrammatic sectional view of one form of a batch-wise antitumor immunocyte-inducing device which is useful for inducing antitumor immunocytes according to the present invention.

When the present invention is used the actual clinical applications, there may be employed, for example, an antitumor immunocyte-inducing device as diagrammatically shown in the accompanying drawing. Referring to the drawing, in this device, an unactivated leucocyte suspension inlet 3 is detachably attached to one open end of a cylindrical container 1 through a first filter 5 spread on the inner side thereof. An activated leucocyte suspension outlet 4 is detachably attached to the other open end of the container 1 through a second filter 5' spread on the inner side thereof. An antitumor immunocyte-inducing material 2 is packed in the container 1 and held between the filters 5 and 5'. To the activated leucocyte suspension outlet 4 is connected a washing unit 6 provided with a third filter 8, an air outlet 9 and a washings outlet 10. The third filter 8 prevents the resulting antitumor immunocytes from going out of the washings outlet 10.

By the use of this device, it is possible to effectively conduct, batchwise, the activation of peripheral blood leucocytes from a patient to induce antitumor immunocytes and the separation, washing and recovery of the induced antitumor immunocytes according to the present invention. For example, leucocytes harvested from patient peripheral blood using a known technique such as continuous centrifugation or the like are poured into the container 1 through the unactivated leucocyte suspension inlet 3 and the first filter 5 to adsorb the leucocytes onto the antitumor immunocyte-inducing material 2. Then, a contact medium saturated with the air containing 5% $CO_2$ is circulated through the inducing material having the leucocytes adsorbed thereon, while maintaining the temperature of the container at 37° C. to induce antitumor immunocytes. The washing unit 6 is detachably attached to the container. While suctioning the air through the air outlet 9 using an aspirator, a washing liquid is allowed to flow down through the unactivated leucocyte suspension inlet 3. The induced antitumor immunocytes are separated from the inducing material by the washing liquid. The washing liquid is allowed to flow out of the washings outlet 10 and collected in a vessel (not shown). The antitumor immunocytes separated from the material by the washing liquid are collected in the upper space 7 on the third filter 8. After completion of sufficient washing, the container 1 is detached, and the collected antitumor immunocytes are taken out. The resulting antitumor immunocytes may be used for medical treatment of cancer patients.

The process of producing antitumor immunocytes according to the present invention is not limited to the above-described batchwise process. Antitumor immunocytes may be produced and utilized by a continuous process. For example, in a continuous process, the above-described antitumor immunocyte-inducing device may be used for ectosomatic circulation. In ectosomatic circulation, the blood taken out from the interior of the living body is passed through the antitumor immunocyte-inducing device to induce and separate antitumor immunocytes. The resulting antitumor immunocytes are returned to the interior of the living body. Such ectosomatic circulation may be carried out for about 4 hours a day to attain the desired medical effect.

As is apparent from the foregoing, leucocytes such as those from patient peripheral blood are efficiently activated by the use of a material comprising an insoluble carrier and a ligand linked with the carrier according to the method of the present invention. The reason for this is believed to reside in that the ligand linked with the insoluble carrier binds to membrane proteins which are present on the surfaces of membranes of leucocytes and participate in activation of the leucocytes, thereby causing a capping formation on the membranes of leucocytes. Safe, highly effective antitumor immunocytes are produced by contacting leucocytes with such a material and separating the resulting immunocytes from the material according to the process of the present invention. Antitumor immunocytes according to the present invention are highly useful for research on antitumor immunity in an animal test using mice, rats, rabbits and other animals or the function test of lymphocytes harvested from cancer patients. It is expected that the antitumor immunocytes are also useful for the treatment of gastric cancer, lung cancer, mammary cancer, liver cancer and other cancers.

Detailed Description of the Preferred Embodiments

The present invention will now be described in detail with reference to the following Examples.

EXAMPLE 1

An insoluble, antitumor immunocyte-inducing material was prepared as follows. In accordance with the teachings described in Pharmacia Fine Chemicals Catalogue 84, p. 14 (published by Pharmacia Fine Chemicals AB,Sweden), various T lymphocyte-activating substances as shown in Table 1 each were separately linked with CNBr-activated Sepharose 6MB having a particle diameter of 250 to 350$\mu$m (manufactured and sold by Pharmacia Fine Chemicals AB, Sweden), as an insoluble carrier, followed by blocking the unreacted active groups with glycine to obtain reaction mixtures. Each of the reaction mixtures thus obtained was subjected to decantation to obtain a supernatant and an antitumor immunocyte-inducing material. Each material thus obtained was repeatedly washed with 0.1 M acetate buffer (pH 4) and 0.1 M sodium carbonate buffer (pH 8.5) by turns, and further washed with a physiological saline. The thus washed materials were used for inducing antitumor immunocytes after removing the water from the materials. The amount of a T lymphocyte-activating substance linked with the insoluble carrier per ml of the insoluble carrier in the wet state was calcutated by the following equation and the results are shown in Table 1.

$$A=(B-C)/D$$

[wherein A is an amount (mg) of a T lymphocyte-activating substance linked with an insoluble carrier per ml of the insoluble carrier in the wet state, B is an amount (mg) of the T lymphocyte-activating substance which was added, C is an amount (mg) of the T lymphocyte-activating substance contained in the supernatant of the reaction mixture and in the washings and D is an amount (ml) of the insoluble carrier]

The terminology "insoluble carrier in the wet state" means an insoluble carrier obtained by immersing an insoluble carrier in a physiological saline (a 0.9 wt. % aqueous NaCl solution) at 20° C. until the insoluble carrier comes to equiliblium with the solution (until the insoluble carrier is sufficiently swollen). The terminology "insoluble carrier in the wet state" is hereinafter referred to simply as "ml of insoluble carrier" or "ml-carrier". The amount of a T lymphocyte-activating substance contained in the supernatant of the reaction mixture and in the washings was determined by measuring the absorbance (at 280 nm) of the supernatant and the washings.

Human leucocytes were obtained as follows. Human peripheral blood collected from a normal human being was diluted 1:2 with Hanks' solution and layered over Ficoll-Paqhe solution (manufactured and sold by Pharmacia Fine Chemicals AB, Sweden) in a centrifuge tube, followed by centrifugation at 2,000 rpm for 20 minutes [Ficoll-Paque centrifugation method (Pharmacia Fine Chemicals Catalogue 84, p. 90)], thereby to form a leucocyte layer as an intermediate layer in the cetrifuge tube. The leucocyte layer was taken out and the leucocytes in the layer were separated and washed with Hanks' solution.

The thus obtained leucocytes were suspended in RPMI 1640 medium (menufactured and sold by Nissui Pharmaceutical Co., Ltd., Japan) containing 10 (v/v)% autologous serum in an amount of $2\times10^6$ cells/ml. One ml of the thus obtained suspension was added to each of 2-ml wells for incubating cells (Falcon No. 3047, manufactured and sold by Falcon, U.S.A.). Then, 20 $\mu$l of each of the above-obtained antitumor immunocyte-inducing materials was added to the respective well and incubated at 37° C. in a $CO_2$ incubator. About one hour later, it was observed that leucocytes adhered to the surface of the insoluble material. The incubation was effected for 24 hours in total, thereby to induce antitumor immucocytes. The thus induced antitumor immunocytes were excellent in cytotoxic activity against tumor cells as shown in the following Examples.

EXAMPLE 2

Human leucocytes obtained in the same manner as described in Example 1 were suspended in RPMI 1640 medium (manufactured and sold by Nissui Pharmaceutical Co., Ltd., Japan) containing 10 (v/v) % autologous serum in an amount of $2\times10^6$ cells/ml. One ml of the thus obtained suspension was added to each of 2-ml wells for incubating cells (Falcon No. 3047, manufactured and sold by Falcon, U.S.A.). Then, 20 $\mu$l of each of the antitumor immunocyte-inducing materials prepared in Example 1 was added to the respective well and incubated at 37° C. in a $CO_2$ incubator. After the incubation was effected for 24 hours, each of the resulting mixtures in the wells was gently drawn in and out of a Pasteur pipette (this operation is hereinafter often referred to as "pipetting"), to thereby agitate the mixture and separate the antitumor immunocytes from the surface of the antitumor immunocyte-inducing material. Then, the mixtures were allowed to stand so that the antitumor immunocyte-inducing materials settled on the bottom, with the antitumor immunocytes suspended in the supernatant. The supernatant was taken out and the antitumor immunocytes in the supernatant were collected and washed with Hanks' solution, to thereby obtain antitumor immunocytes. The thus obtained antitumor immunocytes were suspended in RPMI 1640 medium containing 10 (v/v) % autologous serum in an amount of $5\times10^6$ cells/ml.

The antitumor immunocyte-inducing capacity of the antitumor immunocyte-inducing materials was evaluated in terms of cytotoxic activity of the induced antitumor immunocytes against tumor cells. The cytotoxic activity of the antitumor immunocytes against tumor cells was evaluated as follows. In evaluation, various tumor cell lines which adhere to a plate and proliferate are generally used as a target. In this Example, human mammary carcinoma ZR75-30 and human gastric cancer MKN-1 were used as the target. The cells of each human tumor cell line were suspended in RPMI 1640 medium containing 10 (v/v) % fetal calf serum in an amount of $5 \times 10^4$ cells/ml. 10 μl of the thus obtained suspension was put into a 10 μl-Terasaki plate, followed by incubation in a $CO_2$ incubator at 37° C. for 24 hours. After completion of the incubation, the tumor cells tightly adhered to the bottom of the plate. The tumor cells adhering to the bottom of the plate were washed with the same medium. To the washed tumor cells was added 10 μl of the suspension containing the antitumor immunocytes, followed by incubation in a $CO_2$ incubator at 37° C. for 4 hours, thereby to cause lysis of the tumor cells. The tumor cells lysed by the antitumor immunocytes lost their adhering ability to the plate and were removed together with the antitumor immunocytes by washing with the Hanks' solution. The surviving tumor cells from the lysis remained adhered to the bottom of the plate. The remaining tumor cells were fixed by acetone and stained with Giemsa staining solution. Then, the number of the stained tumor cells was counted under a microscope.

On the other hand, as a control, substantially the same procedures as described above with respect to evaluation of the cytotoxic activity of the antitumor immunocytes against tumor cells were repeated, except that the antitumor immunocytes were not added to the plate to which tumor cells adhered. The cytotoxic activity was calculated by the following equation:

$$\text{Cytotoxic activity (\%)} = \left(1 - \frac{E}{F}\right) \times 100$$

(wherein E is the number of the stained tumor cells surviving from the lysis, and F is the number of the stained tumor cells of control). The results are shown in Table 1 below.

TABLE 1

| Ligand linked with Sepharose 6MB | | Cytotoxic activity against tumor cells (%) | |
|---|---|---|---|
| Kind | Amount (mg/ml-carrier) | Human mammary carcinoma ZR75-30 | Human gastric cancer MKN-1 |
| PHA | 3.0 | 72 | 75 |
| Con A | 2.7 | 34 | 27 |
| WFA | 3.0 | 78 | 65 |
| LCH | 2.1 | 60 | 55 |
| PWM | 2.5 | 76 | 70 |
| SBA | 2.0 | 15 | 20 |
| SJA | 1.1 | 10 | 25 |
| Protein A | 2.3 | 65 | 63 |

As is apparent from Table 1, when human peripheral blood leucocytes were contacted separately with each of insoluble, antitumor immunocyte-inducing materials comprising CNBr-activated Sepharose 6MB and, respectively linked therewith as a ligand, PHA, WFA, LCH, PWM and Protein A, there were induced antitumor immunocytes which were extremely excellent in cytotoxic activity against cells of human tumor cell lines.

COMPARATIVE EXAMPLE 1

$2 \times 10^6$ peripheral blood leucocytes were suspended in 1 ml of RPMI 1640 medium (manufactured and sold by Nissui Pharmaceutical Co., Ltd., Japan) containing 10 (v/v) % autologous serum and incubated at 37° C. in a $CO_2$ incubator for 24 hours without the addition of any antitumor immunocyte-inducing material. No antitumor immunocyte was induced.

Further, $2 \times 10^6$ peripheral blood leucocytes were suspended in 1 ml of RPMI 1640 medium (manufactured and sold by Nissui Pharmaceutical Co., Ltd., Japan) containing 10 (v/v) % autologous serum. To the obtained suspension was added 20 μl of CNBr-activated Sepharose 6MB having a particle diameter of 250 to 350 μm (manufactured and sold by Pharmacia Fine Chemicals AB, Sweden) to which no ligand was linked. Then, the obtained mixture was incubated at 37° C. in a $CO_2$ incubator for 24 hours. No antitumor immunocyte was induced.

COMPARATIVE EXAMPLE 2

$2 \times 10^6$ peripheral blood leucocytes were suspended in 1 ml of RPMI 1640 medium (manufactured and sold by Nissui Pharmaceutical Co., Ltd., Japan) containing 10 (v/v) % autologous serum. To the obtained suspension was added PHA (not linked with a carrier) in an optimum amount (10 μg/ml) and the obtained mixture was incubated at 37° C. in a $CO_2$ incubator for 24 hours. The cytotoxic activity against tumor cells of the thus obtained antitumor immunocytes was determined in the same manner as in Example 2 using human mammary carcinoma ZR75-30 as the target. As a result, it was observed that the antitumor immunocytes showed a cytotoxic activity against tumor cells of 60%. On the other hand, as is shown in Table 1 above, when PHA-linked Sepharose 6MB was used instead of PHA and human mammary carcinoma ZR75-30 were used as the target, the cytotoxic activity against tumor cells was 72%. This shows that when a PHA-linked Sepharose 6MB is used instead of PHA, the capacity of PHA for inducing antitumor immunocytes having cytotoxic activity against tumor cells is not lowered but increased.

EXAMPLE 3

In this Example, $^{125}$I-labelled PHA was employed as a ligand. $^{125}$I-labelled PHA was prepared by the known method [McConahey; Int. Arch. Allergy, 29, 85(1966)] as follows. 2 mg of PHA (manufactured and sold by EY Laboratories, Inc., U.S.A.), 1 mCi of $^{125}$I and chloramine-T (manufactured and sold by Sigma Chemical Company) were mixed on an ice bath. To the mixture were added $NaHSO_4$ and an aqueous KI solution and the resulting mixture was allowed to react. After completion of the reaction, the thus obtained reaction mixture was subjected to gel chromatography to remove unreacted $^{125}$I, and PHA fractions were collected and concentrated. The specific activity of the thus obtained $^{125}$I-labelled PHA was $2 \times 10^5$ cpm/mg.

In substantially the same manner as in Example 1, the $^{125}$I-labelled PHA was linked with 2 g of CNBr-activated Sepharose 6MB as an insoluble carrier and the unreacted active groups in the CNBr-activated Sepharose 6MB were blocked by glycine to obtain a reaction mixture. The reaction mixture thus obtained was subjected to decantation to obtain a supernatant and an insoluble, antitumor immunocyte-inducing material. The thus obtained material was washed with 0.1 M acetic acid buffer (pH 4.0) and then with 0.1 M sodium carbonate buffer (pH 8.5) repeatedly to an extent that the washings showed no radioactivity. The thus washed material was used for inducing antitumor immunocytes after removing the water from the material. The amount of $^{125}$I-labelled PHA linked with the carrier was 50 μg ($10^4$cpm)/ml of the carrier.

Human leucocytes obtained in the same manner as described in Example 1 were suspended in RPMI 1640 medium containing 10 (v/v) % autologous serum in an amount of $2 \times 10^6$ cells/ml (the thus obtained suspension is hereinafter often referred to as "normal human leucocyte suspension"). To 1 ml of the thus obtained suspension was added 100 μl of the above-obtained antitumor immunocyte-inducing material and incubated in substantially the same manner as in Example 1 to obtain antitumor immunocytes.

The cytotoxic activities of the thus obtained antitumor immunocytes against tumor cells were evaluated in substantially the same manner as in Example 2 using human mammary carcinoma ZR75-30 and human gastric cancer MKN-1 as the target. As a result, it was found that the cytotoxic activities of the above-obtained antitumor immunocytes against human mammary carcinoma ZR75-30 was 72% and that against human gastric cancer MKN-1 was 75%.

The radioactivity of the obtained antitumor immunocytes ($1 \times 10^7$) was 52 cpm, i.e., almost the same as that of the background (50 cpm). This shows that the obtained antitumor immunocytes were not contaminated with the ligand (PHA) and that the obtained antitumor immunocytes can be safely administered to a patient with a malignant tumor.

COMPARATIVE EXAMPLE 3

Substantially the same procedures as in Example 3 were repeated to obtain antitumor immunocytes, except that 10 μg of $^{125}$I-labelled PHA ($2 \times 10^3$ cpm) was added, instead of 100 μl of the Sepharose 6MB with which $^{125}$I-labelled PHA was linked, to 1 ml of the normal human lecucoyte suspension. The thus obtained antitumor immunocytes ($1 \times 10^7$) exhibited a radioactivity of 500 cpm (background: 50 cpm). This shows that the obtained antitumor immunocytes were contaminated with the ligand (PHA).

EXAMPLE 4

2 g of swine gastric mucosa mucin (manufactured and sold by Sigma Chemical Company) was added to 20 ml of 0.2 N aqueous NaOH solution. The resulting mixture was kept at 37° C. for 24 hours to decompose the mucin. Thereafter, a special grade ethanol was added to the solution so that the amount of ethanol in the solution became 60 (v/v) %. Thus, the mucin remaining undecomposed was precipitated. The resulting supernatant was harvested and vacuum-evaporated to dryness. The above-obtained solids were dissolved in 5 ml of 0.2 M phosphoric acid buffer (pH 8.0) and subjected to gel chromatography using as packing material Sephadex G-50 (manufactured and sold by Pharmacia Fine Chemicals AB, Sweden). The sugar concentration of each of the obtained fractions was determined by the phenol-sulfuric acid method, and oligosaccharide fractions having molecular weights of 500 to 2000 were collected and concentrated. By the above-mentioned procedures, 20 mg of oligosaccharide was obtained from 2 g of the mucin. 10 mg of the thus obtained oligosaccharide was linked with 2 ml of an epoxy-activated Sepharose (manufactured and sold by Pharmacia Fine Chemicals AB, Sweden) by the method described in a pamphlet enclosed in a package of Sepharose.

Thus, an antitumor immunocyte-inducing material was obtained.

Normal human leucocytes were obtained in the same manner as in Example 1. The thus obtained leucocytes were suspended at a cell concentration of $2 \times 10^6$/ml in RPMI 1640 medium containing 10 (v/v) % autologous serum. One ml of the thus obtained suspension was added to each of 2-ml wells for incubating cells (Falcon No. 3047, manufactured and sold by Falcon, USA). 50 μl of the above-prepared antitumor immunocyte-inducing material was added to each well and incubated at 37° C. for 3 days in a $CO_2$ incubator. After the incubation, each of the resulting mixtures was subjected to pipetting. Thus, the mixture was agitated and antitumor immunocytes were separated from the surface of the antitumor immunocyte-inducing material. Then, the mixture was allowed to stand so that the antitumor immunocyte-inducing materials settled on the bottom, with the antitumor immunocytes suspended in the supernatant. The supernatant was taken out and the antitumor immunocytes in the supernatant were collected and washed with Hanks' solution, thereby to obtain antitumor immunocytes. The thus obtained antitumor immunocytes were suspended in RPMI 1640 medium containing 10 (v/v) % autologous serum in an amount of $5 \times 10^6$ cells/ml. The cytotoxic activity against MKN-1 was determined in substantially the same manner as in Example 2, except that the above-obtained antitumor immunocytes were used instead of the antitumor immunocytes obtained in Example 2. The cytotoxic activity of the above-obtained antitumor immunocytes was 50%.

EXAMPLE 5

An oligosaccharide having the following structure was synthesized by the customary method ["Shin Jikken Kagaku Kouza (Lecture on New Experimental Chemistry)", Vol. 14, No. 5, page 2468, Maruzen K.K., Japan, 1978].

10 mg of the thus synthesized oligosaccharide was linked with 2 ml of the epoxy-activated Sepharose (manufactured and sold by Pharmacia Fine Chemicals AB, Sweden) in substantially the same manner as in Example 4, thereby to obtain an insoluble, antitumor immunocyte-inducing material. Antitumor immunocytes were obtained in substantially the same manner as in Example 4, except that the above-obtained antitumor immunocyte-inducing material was used instead of the antitumor immunocyte-inducing material used in Example 4. Then, the cytotoxic activity of the above-obtained antitumor immunocytes was evaluated in substantially the same manner as in Example 3, except that human lung cancer PC-10 was used as the target instead of human mammary carcinoma ZR75-30 and human gastric cancer MKN-1. As a result, it was found that the cytotoxic activity of the antitumor immunocytes was 62%.

Substantially the same procedures as mentioned above were repeated to prepare a $^{14}C$-labelled antitumor immunocyte-inducing material, except that a $^{14}C$-labelled oligosaccharide was used instead of the above-used unlabelled oligosaccharide. Antitumor immunocytes were obtained in substantially the same manner as mentioned above, except that the above-prepared $^{14}C$-labelled antitumor immunocyte-inducing material was used instead of the unlabelled antitumor immunocyte-inducing material. The radioactivity of the antitumor immunocytes obtained by using the antitumor immunocyte-inducing material was measured in the same manner as in Example 3. As a result, it was found that the antitumor immunocytes obtained by using the antitumor immunocyte-inducing material contained no ligand (oligosaccharide).

EXAMPLE 6

An insoluble, antitumor immunocyte-inducing material was prepared as follows. A homogeneous liquid mixture of 100 g of vinyl acetate, 64.3 g of triallyl isocyanurate (degree of crosslinking: 0.40), 100 g of ethyl acetate, 100 g of heptane, 7.5 g of polyvinyl acetate (polymerization degree : 500) and 3.8 g of 2,2'-azobisisobutyronitrile and 400 ml of an aqueous solution containing 1% by weight of polyvinyl alcohol, 0.05% by weight of sodium dihydrogenphosphate dihydrate and 1.5% by weight of disodium hydrogenphosphate dodecahydrate were charged in a flask. The mixture was sufficiently stirred and heated at 65° C. for 18 hours and at 75° C. for 5 hours to effect suspension polymerization. Thus, there was obtained a granular copolymer. The obtained copolymer was washed with water and then with acetone. Thereafter, the copolymer was subjected to an ester interchange reaction in a solution of 46.5 g of sodium hydroxide and 2 liters of methanol at 40° C. for 18 hours. Thus, there was obtained a gel having an average particle diameter of 150 μm, a hydroxyl group density of 9.0 meq/g, a specific surface area of 60 $m^2/g$ and an exclusion limit of molecular weight, in terms of a value as measured using dextran, of $6 \times 10^5$. The gel was epoxy-activated by the epichlorohydrin method [Ichiro Senhata, "Affinity Chromatography", Kodansha Scientific, p. 71 (1976)] to obtain an epoxy-activated gel. The thus obtained epoxy-activated gel was used as an insoluble carrier. To aliquots of the epoxy-activated gel were separately added; twice volumes of 5% aqueous potassium hydroxide solutions respectively containing 50 mM of a nucleic acid-constituting base as indicated in Table 2, followed by shaking at 50° C. for 24 hours, thereby to effect linking of the nucleic acid-constituting bases with the aliquots of the epoxy-activated gel. Each of the reaction mixtures thus obtained was subjected to decantation to obtain a supernatant and an insoluble, antitumor immunocyte-inducing material. Each material thus obtained was washed repeatedly with 0.1 M acetate buffer (pH 4.0) and 0.1 M sodium carbonate buffer (pH 8.5) by turns and washed with a physiological saline. The washed material was sterilized using an autoclave. The amount of the nucleic acid-constituting base linked with the insoluble carrier was calculated by the following equation and the results are shown in Table 2.

$$G = (H - I)/J$$

[wherein G is an amount (μmol) of a nucleic acid-constituting base linked with an insoluble carrier per ml of the insoluble carrier, H is an amount (μmol) of a nucleic acid-constituting base which was added to an insoluble carrier, I is an amount (μmol) of a nucleic acid-constituting base contained in the supernatant of the reaction mixture and in the washings and J is an amount (ml) of an insoluble carrier]. The amount of an nucleic acid-constituting base in the supernatant of the reaction mixture and in the washings was determined by measuring the absorbance (at 260.5 nm for adenine, 276 nm for guanine, 267 nm for cytosine and 265 nm for thymine) of the supernatant and the washings.

Human peripheral blood lymphocytes obtained in the same manner as in Example 1 were suspended in RPMI 1640 medium (manufactured and sold by Nissui Pharmaceutical Co., Ltd., Japan) containing 10 (v/v) % autologous serum in an amount of $2 \times 10^6$ cells/ml. One ml of the thus obtained suspension was put into each of 2 ml-wells for incubating cells (Falcon No. 3047, manufactured and sold by Falcon, U.S.A.). Then, 100 μl of each of the above-obtained antitumor immunocyte-inducing materials was added to the respective well and incubated at 37° C. for 4 days in a $CO_2$ incubator, thereby to induce antitumor immunocytes. After completion of the incubation, the resulting mixture was subjected to pipetting to separate the antitumor immunocytes from the antitumor immunocyte-inducing material. The mixture was then allowed to stand so that the antitumor immunocyte-inducing material settled, with the antitumor immunocytes suspended in the supernatant. The supernatant of the mixture was taken out and the antitumor immunocytes suspended in the supernatant were collected and washed with Hanks' solution. The thus obtained antitumor immunocytes were suspended in RPMI 1640 medium containing 10 (v/v) % autologous serum in an amount of $5 \times 10^6$ cells/ml.

The antitumor immunocyte-inducing capacity of the antitumor immunocyte-inducing material was evaluated in terms of the cytotoxic activity of the induced antitumor immunocytes against tumor cells. The cytotoxic activity of the antitumor immunocytes against tumor cells was evaluated in substantially the same manner as in Example 2, except that human lung cancer PC-10 was used as the target instead of human mammary carcinoma ZR75-30. The results are in Table 2.

TABLE 2

| Ligand linked with insoluble carrier | | Cytotoxic activity againtst tumor cells (%) | |
|---|---|---|---|
| Kind | Amount (μmol/ml-carrier) | Human gastric cancer MKN-1 | Human lung cancer PC-10 |
| Adenine | 60 | 62 | 65 |
| Guanine | 30 | 60 | 58 |
| Cytosine | 40 | 30 | 28 |
| Thymine | 30 | 26 | 30 |

Substantially the same procedures as mentioned above were repeated to prepare $^{14}C$-labelled antitumor immunocyte-inducing materials, except that $^{14}C$-labelled nucleic acid-constituting bases were used instead of the above-used unlabelled nucleic acid-constituting bases. The $^{14}C$-labelled nucleic acid-constituting bases were prepared by the customary method [McConahey; Int. Arch. Allergy, 29, 185 (1966)]. Antitumor immunocytes were obtained in substantially the same manner as mentioned above, except that the above-prepared $^{14}C$-labelled antitumor immunocyte-inducing materials were used instead of the unlabelled antitumor immunocyte-inducing material. The radioactivity of the antitumor immunocytes obtained by using each antitumor immunocyte-inducing material was measured in the same manner as in Example 3. As a result, it was found that the antitumor immunocytes obtained by using each antitumor immunocyte-inducing material contained no ligand.

COMPARATIVE EXAMPLE 4

$2 \times 10^6$ human peripheral blood leucocytes were suspended in 1 ml of RPMI 1640 medium (manufactured and sold by Nissui Pharmaceutical Co., Ltd., Japan) containing 10 (v/v)% autologous serum. To the obtained suspension was added 200 μl of the epoxy-activated gel which is the same as that used in Example 6 and with which no ligand is linked. Then, the obtained mixture was incubated at 37° C. for 4 days. No antitumor immunocytes were induced.

EXAMPLE 7

1 g of glass beads having an average particle diameter of 120 μm were added to 5 ml of a 20% acetone solution of 3-glycidoxypropyltrimethoxysilane (Tokyo Kasei K.K., Japan). The mixture was heated, while shaking, at 50° C. for 40 hours to bond a cyclic epoxy group to the surface of the glass beads. Then, the resulting glass beads were washed with acetone. With the surface of the glass beads thus obtained were separately linked nucleic acid-constituting bases as indicated in Table 3 in substantially the same manner as in Example 6 to obtain antitumor immunocyte-inducing materials. The amount of the nucleic acid-constituting base linked with the glass beads is shown in Table 3.

Mouse leucocytes were prepared as follows. A spleen taken out of a BALB/c mouse with an age of 6 weeks was pressed to pieces on a stainless steel mesh with pincettes and suspended in Hanks' solution. The suspension was allowed to stand for several minutes to settle spleen tissue fragments, with spleen cells suspended in the supernatant. The supernatant was taken out and subjected to centrifugation at 800 rpm for 10 minutes to collect the spleen cells. The spleen cells were suspended in about 1 ml of a 0.85 (v/v) % aqueous solution of ammonium chloride, and incubated at 37° C. for 2 minutes. Immediately after the incubation, 10 ml of Hanks' solution was added to the suspension, followed by centrifugation at 800 rpm for 10 minutes to obtain mouse leucocytes. The leucocytes were suspended in RPMI 1640 medium containing 10 (v/v) % fetal calf serum in an amount of $5 \times 10^6$ cells/ml. The leucocyte-containing suspension was pipetted by 2 ml into each of several wells for incubating cells (Falcon No. 3047), and the above-obtained antitumor immunocyte-inducing materials were separately added in an amount of 1 g to the wells. The wells were incubated in a CO₂ incubator at 37° C. for 4 days to induce antitumor immunocytes. At the end of the incubation, the resulting mixture in each well was subjected to pipetting to separate the antitumor immunocytes from the surface of the antitumor immunocyte-inducing material. The resulting mixture was allowed to stand still to settle the material, with the antitumor immunocytes suspended in the supernatant. From the supernatants, the antitumor immunocytes were harvested, washed with Hanks' solution and resuspended respectively in RPMI 1640 medium containing 10 (v/v) % fetal calf serum in an amount of $1 \times 10^7$ cells/ml.

The cytotoxic activity of the thus obtained antitumor immunocytes was evaluated in substantially the same manner as in Example 2, except that mouse tumor cell lines (Colon-26 and B-16) were used as the target. Table 3 shows the results.

TABLE 3

| Ligand linked with insoluble carrier | | Cytotoxic activity against tumor cells (%) | |
|---|---|---|---|
| Kind | Amount (μmol/ml-carrier) | BALB/c mouse cancer Colon-26 | C-57/BL-6 mouse cancer B-16 |
| 2-aminoadenine | 70 | 48 | 45 |
| 7-methylguanine | 20 | 42 | 51 |
| Uracil | 20 | 33 | 40 |
| 5-methylcytosine | 30 | 29 | 35 |

Substantially the same procedures as mentioned above were repeated to prepare ¹⁴C-labelled antitumor immunocyte-inducing materials, except that ¹⁴C-labelled nucleic acid-constituting bases were used instead of the above-used unlabelled nucleic acid-constituting bases. Antitumor immunocytes were obtained in substantially the same manner as mentioned above, except that the above-prepared ¹⁴C-labelled antitumor immunocyte-inducing materials were used instead of the unlabelled antitumor immunocyte-inducing materials. The radioactivity of the antitumor immunocytes obtained by using each antitumor immunocyte-inducing material was measured in the same manner as in Example 3. As a result, it was found that the antitumor immunocytes obtained by using each antitumor immunocyte-inducing material contained no ligand.

EXAMPLE 8

Cation exchange resin Diaion PK208.(manufactured and sold by Mitsubishi Kasei Kogyo K.K., Japan) containing sulfonic groups was used as an antitumor immunocyte-inducing material. Diaion PK208 was washed with a physiological saline and subjected to autoclave sterilization at 121° C. for 20 minutes. Mouse leucocytes from a BALB/c mouse spleen were obtained in substantially the same manner as in Example 7, and suspended in RPMI 1640 medium containing 10 (v/v) % fetal calf serum in an amount of $5 \times 10^6$ cells/ml. The leucocyte-containing suspension was pipetted by 2 ml into each of tubes for incubating cells (Falcon No. 2058, manufactured and sold by Falcon, U.S.A.), and to each tube was added 0.2 ml of the above-obtained antitumor immunocyte-inducing material. The tubes were incubated at 37° C. in a CO₂ incubator for 60 hours to induce antitumor immunocytes. At the end of the incubation, the resulting mixture in each tube was subjected to pipetting to separate the antitumor immunocytes from the surface of the antitumor immunocyte-inducing material. The mixture was allowed to stand to settle the material, with the antitumor immunocytes suspended in the supernatant. The supernatant was taken out and the antitumor immunocytes in the supernatant were harvested, washed with Hanks' solution and resuspended in two RPMI 1640 media containing 10 (v/v) % fetal calf serum in respective amounts of $1 \times 10^7$ and $2 \times 10^7$ cells/ml.

The cytotoxic activity of the thus obtained antitumor immunocytes was evaluated in substantially the same manner as in Example 2 except that Colon-26 and B-16 were used as the target. Table 4 shows the results.

TABLE 4

| Cytotoxic activity against Colon-26 (%) | | Cytotoxic activity against B-16 (%) | |
|---|---|---|---|
| E/T* = 200 | E/T* = 400 | E/T* = 200 | E/T* = 400 |
| 55 | 64 | 42 | 57 |

Note:*
$$E/T = \frac{\text{Number of antitumor immunocytes}}{\text{Number of target cells}}$$

EXAMPLE 9

In substantially the same manner as in Example 7, glass beads having an average particle diameter of 100 microns were activated with a cyclic epoxy group. 10 ml of each of 0.1 M carbonate buffers (pH 9.5) respectively containing 100 mg of heparin, dextran sulfate, taurine and polyacrylic acid as a ligand were separately added to each 1 g of the glass beads. The resulting mixtures were heated at 40° C. for 24 hours to link each of the ligands with the glass beads. After completion of the reaction, the cyclic epoxy groups remaining unreacted were blocked by immersing the treated glass beads in 0.1 M glycine-carbonate buffer (pH 9.0) at 40° C. for 24 hours, and the glass beads were then washed with a physiological saline to obtain antitumor immunocyte-inducing materials.

Mouse leucocytes from a BALB/c mouse spleen were prepared in substantially the same manner as in Example 7. The mouse leucocytes were separately suspended, in an amount of $5 \times 10^6$ cells/ml, in each of 10 ml aliquots of RPMI 1640 medium containing 10 (v/v)% fetal calf serum. To the suspensions were respectively added the above-obtained antitumor immunocyte-inducing materials in an amount of 200 μ. The resulting suspensions were incubated in a $CO_2$ incubator at 37° C. for 60 hours. After the incubation, the antitumor immunocytes were separated from the antitumor immunocyte-inducing material in substantially the same manner as in Example 7 to obtain antitumor immunocytes. The cytotoxic activities of the thus obtained antitumor immunocytes were evaluated in substantially the same manner as in Example 2 except that Colon-26 was used as the target and that the numbers of antitumor immunocytes and Colon-26 cells were $1 \times 10^5$ and 500, respectively. Table 5 shows the results.

TABLE 5

| Ligand linked with insoluble carrier | Cytotoxic activity against Colon-26 (%) |
|---|---|
| Heparin | 42 |
| Dextran sulfate | 56 |
| Taurine | 34 |
| Polyacrylic acid | 53 |

EXAMPLE 10

Red kidney bean lectin (PHA, *Phaseolus vulgaris*, EY Laboratories Inc., USA) and anti-Leu2A monoclonal antibody (Becton Dikinson, USA) were respectively linked with CNBr-activated Sepharose 6MBs in substantially the same manner as in Example 1 to obtain an antitumor immunocyte-inducing material and a suppressor T cell-removing material. The amounts of the PHA and anti-Leu2A monoclonal antibody linked with the insoluble carriers were respectively 3 mg/ml and 0.5 mg/ml of the insoluble carrier.

Suppressor T cells were removed in the following manner. Normal human leucocytes were suspended in an amount of $2.5 \times 10^7$ cells/ml in RPMI 1640 medium containing 10 (v/v)% autologous serum. Then, 2 ml of the suspension was charged into a column packed with 5 ml of the suppressor T cell-removing material. The column was maintained at room temperature for 30 minutes. Subsequently, 20 ml of RPMI 1640 medium containing 10 (v/v)% autologous serum was charged into the column to recover the leucocytes which had not been adsorbed onto the suppressor T cell-removing material. It was found that more than 90% of the supplessor T cells were removed, according to the measurement of the recovered unadsorbed leucocytes using FITC-labelled Leu2A monoclonal antibody (Becton Dickinson, USA).

The obtained leucocytes unadsorbed on the removing material were suspended in an amount of $2 \times 10^6$ cells/ml in RPMI 1640 medium containing 10 (v/v)% autologous serum. To 20 ml of the suspension was added 0.5 ml of the above-obtained antitumor immunocyte-inducing material, followed by incubation at 37° C. in a $CO_2$ incubator. About one hour after the initiation of the incubation, adhesion of the leucocytes to the surface of the carrier was observed. Incubation was conducted for 24 hours, and the resulting antitumor immunocytes were separated by pipetting from the surface of the antitumor immunocyte-inducing material. Then, the mixture was allowed to stand to settle the antitumor immunocyte-inducing material and then subjected to decantation to obtain a supernatant. From the supernatant, the antitumor immunocytes were harvested, washed with Hanks' solution, and resuspended in RPMI 1640 medium containing 10 (v/v)% autologous serum in an amount of $5 \times 10^6$ cells/ml.

The cytotoxic activity of the thus obtained antitumor immunocytes was evaluated in the same manner as in Example 2, except that PC-10 was used as the target. The cytotoxic activity was 77%.

Substantially the same procedures as mentioned above were repeated to prepare a $^{125}$I-labelled antitumor immunocyte-inducing material, except that $^{125}$I-labelled PHA was used instead of the above-used unlabelled PHA. Antitumor immunocytes were obtained in substantially the same manner as mentioned above, except that the above-prepared $^{125}$I-labelled antitumor immunocyte-inducing material was used instead of the unlabelled antitumor immunocyte-inducing material. The radioactivity of the thus obtained antitumor immunocytes was measured in the same manner as in Example 3. As a result, it was found that the thus obtained antitumor immunocytes contained no ligand.

EXAMPLE 11

Substantially the same procedures as in Example 10 were repeated, except that the step for removing suppressor T cells was omitted. The cytotoxic activity of the thus obtained antitumor immunocytes was 65%.

EXAMPLE 12

Substantially the same procedures as in Example 10 were repeated to remove monocytes from normal human leucocytes, except that anti-LeuM2 monoclonal antibody (Becton Dickinson, U.S.A.) was employed to remove monocytes from normal human leucocytes instead of antiLeu2A monoclonal antibody employed to remove suppressor T cells from normal human leucocytes. By passing normal human leucocytes through a column packed with anti-LeuM2 monoclonal antibody linked with the CNBr-activated Sepharose 6MB, about 90% of the monocytes were removed. Incidentally, in determining the amount of the monocytes removed, FITC-labelled LeuM2-monoclonal antibody was used.

The treated leucocytes were contacted with the antitumor immunocyte-inducing material prepared in the same manner as in Example 10 to obtain antitumor immunocytes having a cytotoxic antivity of 78%.

Substantially the same procedures as mentioned above were repeated to prepare a $^{125}$I-labelled antitumor immunocyte-inducing material, except that $^{125}$I-labelled PHA was used instead of the above-used unlabelled PHA. Antitumor immunocytes were obtained in substatially the same manner as mentioned above, except that the above-prepared $^{125}$I-labelled antitumor immunocyte-inducing material was used instead of the unlabelled antitumor immunocyte-inducing material. The radioactivity of the thus obtained antitumor immunocytes was measured in the same manner as in EXample 3. As a result, it was found that the thus obtained antitumor immunocytes contained no ligand.

EXAMPLE 13

Except that the step for removing monocytes was omitted, substantially the same procedures as in Example 11 were repeated. The cytotoxic activity of the thus obtained antitumor immunocytes was 67%.

EXAMPLE 14

Mouse leucocytes originating from a BALB/c mouse spleen were obtained in substantially the same manner as in Example 7. The mouse leucocytes were suspended in an amount of $5 \times 10^6$ cells/ml in RPMI 1640 medium containing 10(v/v)% fetal calf serum. To the resulting suspension was added PWM-linked Sepharose 6MB prepared in Example 1 in an amount of 50 μl/ml. The suspension was pipetted into 2-ml wells for incubating cells (Falcon No.3047), followed by incubation in a $CO_2$ incubator at 37° C. for 3 days to induce antitumor immunocytes. After the incubation, the antitumor immunocytes were obtained in substantially the same manner as in Example 2.

50 μl of a physiological saline containing $1 \times 10^4$ cells of a syngeneic tumor Colon-26 originating from a BALB/c mouse and $2 \times 10^6$ antitumor immunocytes were subcutaneously injected into five BALB/c mice. After the injection, the mice were checked for tumor generation. As a result, no tumor generation was observed in all five mice, and the five mice were alive more than 150 days from the injection. That is, multiplication of the syngeneic tumor was completely inhibited, when tumor cells were injected into the syngeneic mice together with the antitumor immunocytes of the present invention.

Substantially the same procedures as mentioned above were repeated to prepare a $^{125}$I-labelled antitumor immunocyte-inducing material, except that $^{125}$I-labelled PWM was used instead of the above-used unlabelled PWM. Antitumor immunocytes were obtained in substantially the same manner as mentioned above, except that the above-prepared $^{125}$I-labelled antitumor immunocyte-inducing material was used instead of the unlabelled antitumor immunocyte-inducing material. The radioactivity of the antitumor immunocytes obtained by using the antitumor immunocyte-inducing material was measured in the same manner as in Example 3. As a result, it was found that the antitumor immunocytes obtained by using the antitumor immunocyte-inducing material contained no ligand.

COMPARATIVE EXAMPLE 5

50 μl of a physiological saline containing $1 \times 10^4$ Colon-26 tumor cells but no antitumor immunocytes was hypodermically injected into five BALB/c mice. As a result, tumor generation was observed in all five mice, and all of them died 30-40 days from the injection.

EXAMPLE 15

An antitumor immunocyte-inducing device was assembled as shown in FIG. 1. The diameter and length of the column were 1 cm and 6 cm, respectively. 3 ml of PHA-linked Sepharose 6MB as prepared in Example 1 was suspended in 2 ml of RPMI 1640 medium containing 10 (v/v) % autologous serum and the suspention was charged in the column. $1 \times 10^7$ normal human leucocytes obtained in substantially the same manner as in Example 1 were suspended in 1 ml of RPMI 1640 medium containing 10 (v/v) % autologous serum, and the suspension was supplied into the column through the upper inlet.

Incubation was effected at 37° C. for 24 hours while circulating RPMI 1640 medium containing 10 (v/v) % autologous serum and 5 (w/w) % $CO_2$, at a circulation rate of 1 ml/hr to induce antitumor immunocytes. After the incubation, the antitumor immunocytes were separated by pipetting from the surface of the antitumor immunocyte-inducing material. Then, the washing unit was connected to the cylindrical container. While pouring a physiological saline into the column, suction filtration was effected to collect $6 \times 10^6$ antitumor immunocytes.

The cytotoxic activity of the thus obtained antitumor immunocytes against human mammary carcinoma ZR75-30 was evaluated in the same manner as in Example 2. The cytotoxic activity was 75%.

Substantially the same procedures as mentioned above were repeated to prepare a $^{125}$I-labelled antitumor immunocyte-inducing material, except that $^{125}$I-labelled PHA was used instead of the above-used unlabelled PHA. Antitumor immunocytes were obtained in substantially the same manner as mentioned above, except that the above-prepared $^{125}$I-labelled antitumor immunocyte-inducing material was used instead of the unlabelled antitumor immunocyte-inducing material. The radioactivity of the antitumor immunocytes obtained by using the antitumor immunocyte-inducing material was measured in the same manner as in Example 3. As a result, it was found that the antitumor immunocytes obtained by using the antitumor immunocyte-inducing material contained no ligand.

What is claimed is:

1. A process for producing T cells cytotoxic to tumor cells comprising:

contacting leucocytes comprising T cells not cytotoxic to tumor cells with a water-insoluble material which binds to and induces T cells, said material comprising a water-insoluble carrier and a ligand covalently bonded to the surface of said carrier on its surface by means of a covalent bond wherein said ligand converts said T cells to activated T cells cytotoxic to tumor cells, for a time and under conditions sufficient to induce T cells cytotoxic to tumor cells, thereby converting said T cells to activated T cells cytotoxic to tumor cells; and separating said leucocytes comprising said activated T cells from said water-insoluble, material, thus obtaining said activated T cells in substantially ligand-free form.

2. A process according to claim 1, wherein said ligand is a member selected from the group consisting of a T lymphocyte-activating substance, an antigenic substance, a hydrophobic substance and an anionic substance.

3. A process according to claim 2, wherein said T lymphocyte-activating substance is a lectin or a protein A.

4. A process according to claim 2, wherein said antigenic substance is an oligosaccharide.

5. A process according to claim 2, wherein said hydrophobic substance is a compound having at least one aromatic ring.

6. A process according to claim 5, wherein said compound having at least one aromatic ring is a chemically modified or unmodified nucleic acid-constituting base.

7. A process according to claim 1, wherein the leucocytes are ones which have been subjected to an immunosuppressor cell-removing treatment.

8. A process according to claim 7, wherein the immunosuppressor cells are at least one member selected from the group consisting of suppressor T cells and suppressor macrophages.

* * * * *